United States Patent [19]

Wunderlich et al.

[11] Patent Number: 5,556,638
[45] Date of Patent: Sep. 17, 1996

[54] FLURBIPROFEN-CONTAINING IMMEDIATE-EFFECT MEDICAMENT AND ITS USE

[75] Inventors: Jens-Christian Wunderlich, Heidelberg; Otto Schuster, Bad Soden; Helmut Lukas, Neu-Isenburg; Ursula Schick, Schriesheim, all of Germany

[73] Assignee: Alfatec Pharma GMBH, Heidelberg, Germany

[21] Appl. No.: 244,614

[22] PCT Filed: Dec. 4, 1992

[86] PCT No.: PCT/DE92/01008

§ 371 Date: Sep. 16, 1994

§ 102(e) Date: Sep. 16, 1994

[87] PCT Pub. No.: WO93/10766

PCT Pub. Date: Jun. 10, 1993

[30] Foreign Application Priority Data

Dec. 5, 1991 [DE] Germany .................. 41 40 184.0

[51] Int. Cl.$^6$ .................. A61K 9/51; A61K 31/19

[52] U.S. Cl. .................. 424/468
[58] Field of Search .................. 424/468

[56] References Cited

U.S. PATENT DOCUMENTS 4,888,178 12/1989 Rotini et al. .................. 424/468

Primary Examiner—Marianne M. Cintins
Assistant Examiner—Keith MacMillan
Attorney, Agent, or Firm—Burns, Doane, Swecker & Mathis, L.L.P.

[57] ABSTRACT

A medicament for immediately treating painful, inflammatory and/or febrile acute diseases contains flurbiprofen as a racemate, a mixture of a racemate with its enantiomers, a pseudoracemate (mixtures of equal parts of S- and R-flurbiprofen) or as a mixture of different parts of S- and R-flurbiprofen in the range extending between pure S and pure R-flurbiprofen as active substance in the form of a pharmaceutically applicable nanosol. This medicament satisfies all requirements of an immediate-effect pharmaceutic form.

20 Claims, 2 Drawing Sheets

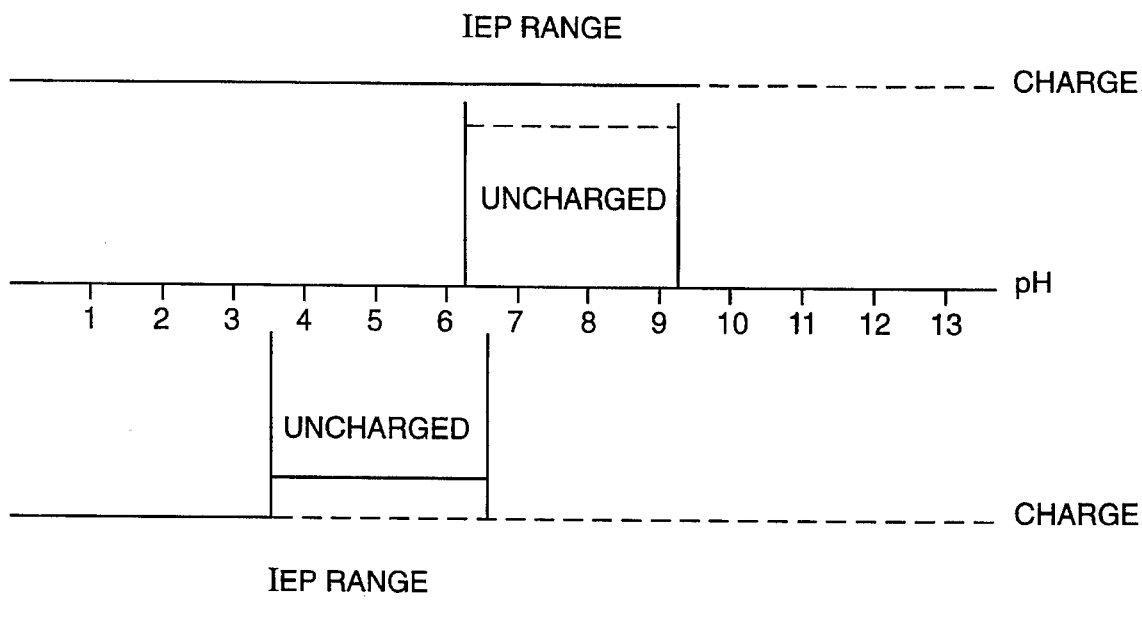
FIG._1

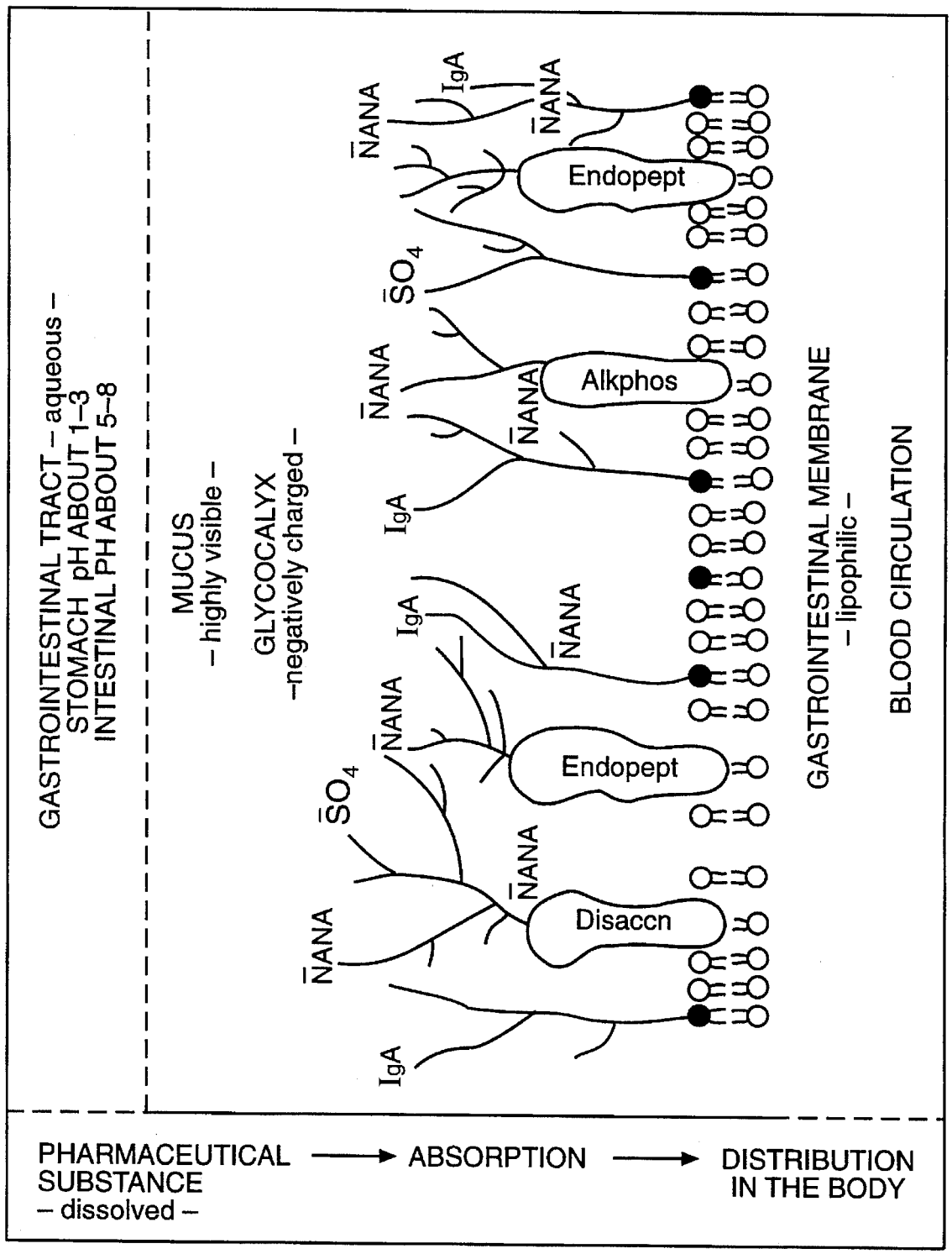
FIG._2

FLURBIPROFEN-CONTAINING IMMEDIATE-EFFECT MEDICAMENT AND ITS USE

This application is a 371 of PCT/DE92/01008, filed Dec. 4, 1992.

The invention relates to an immediate-effect medicament for the treatment of painful and/or inflammatory and febrile disorders, which contains flurbiprofen in addition to customary pharmaceutical excipients and auxiliaries, wherein the flurbiprofen is present in the form of a pharmaceutically administrable nanosol which, as excipient, essentially contains gelatin, a collagen hydrolyzate or a gelatin derivative, the nanosol a) having an inner phase of flurbiprofen which has a particle size of 10–800 nm and possesses a surface charge, b) an outer phase of gelatin, a collagen hydrolyzate or a gelatin derivative, which is oppositely charged, and c) an approximately or completely isoionic charge state of the inner and outer phase and d) being physiologically absorbable.

The invention furthermore relates such a medicament which is present partially as an immediate-effect form and partially as a sustained-release form, and the use of a pharmaceutically administrable nanosol of flurbiprofen, which is present to more than 50% as S- or R-flurbiprofen, for the preparation of an analgesic and/or antirheumatic and/or antipyretic having an immediate effect.

Nonsteroidal antirheumatics are proven substances in the therapy of rheumatic disorders and in the symptomatic therapy of pain and of fever. The common mechanism of action for analgesia, the anti-inflammatory action and the antipyretic action is based on the inhibition of prostaglandin synthesis.

The 2-arylpropionic acid derivative flurbiprofen (2-(2-fluoro-4-biphenylyl)propionic acid $C_{15}H_{13}FO_2$) having the following structure

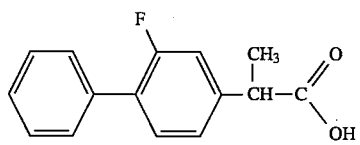

is of particular importance as a representative of this indication group because of its relatively low individual dose of 50 or 100 mg compared with its structural relatives, such as e.g. ibuprofen. Fundamentally, it can be said that a development in the dose reduction trend also comprises an optimization of the medicament safety. The findings of pharmacological research verify that the effective potential of this substance can additionally be increased to an appreciable extent by the use of its optical antipodes:

To be precise, it was found that a pronounced analgesic action is to be ascribed to R-flurbiprofen and a marked anti-inflammatory action to S-flurbiprofen. This finding makes possible selective use in therapy. A further dose reduction accompanies this with the same activity, so that individual-dose immediate-effect forms containing 25, 50 and 100 mg of R- or S-flurbiprofen can be called the painkillers of the future.

In the customary, non-stereospecific synthesis flurbiprofen is formed as a racemate. It is known that the racemate has significant undesirable side effects. The use of the enantiomerically pure flurbiprofens also makes possible, in addition to the lowering of the dose, the reduction of undesirable effects. Since the introduction of large-scale production processes for the enantiomerically pure substances, nothing more now stands in the way of extensive therapeutic use.

The following interesting view is a point in the favor of the use of pseudoracemates of flurbiprofen:

A synthetic mixture (pseudoracemate, mixed from 50% each of the S- and the R-enantiomer) of flurbiprofen behaves with respect to its dissolution rate (release) in aqueous medium differently than the racemic flurbiprofen, consisting of 50% each of S- and R-enantiomer, obtained in the customary synthesis. Actually, the dissolution rate of the pseudoracemate is substantially higher than that of the racemate. As a result of this, investigations show that after administration of the pseudoracemate substantially higher blood levels were achieved than after administration of the racemate.

In spite of all efforts, however, there has still been no success in developing a pharmaceutical formulation for flurbiprofen which fulfills all requirements of an immediate-effect form having a rapid influx.

Racemic flurbiprofen having a solubility of 32.5 mg per liter of water, its enantiomers, the pseudoracemate and mixtures of the enantiomers in different proportions are amongst the poorly soluble substances. It is known according to the general theories of absorption that active compounds are absorbed in the body only in dissolved and undissociated form. For pharmaceutical formulation to give a pharmaceutical form, this fact must therefore be taken into account because problematic bioavailability results from the poor solubility.

A common method of overcoming this problem is the micronization of active compounds. In this method, it is attempted according to the Noyes-Whitney equation to reduce the particle size, which should cause an increase in the effective active compound surface area A. As a result the bioavailability is improved. Thus it is also customary to employ micronized powders for poorly soluble analgesics/antirheumatics.

The technique of micronization is energy-consuming and expensive and problems occur with very fine dusts, such as e.g. the danger of a dust explosion and the danger of dust inhalation by the personnel, which necessitates extensive protective measures. On account of electrostatic charge, the powder itself is difficult to process with respect to flow properties and is usually poorly wettable (aerophilicity). As a result of the high preparation costs, the price for micronized powder is substantially higher than for conventional powders.

However, in the small intestine, where flurbiprofen is preferably absorbed, in order to guarantee an adequate rate of solution micronization is the method of choice.

It has been shown that minimization of the gastrointestinal side effects merely by the use of enantiomerically pure active compounds alone is still not satisfactory because, in addition to the poor solubility, flurbiprofen, both the racemate and the pure enantiomers or mixtures thereof, as an active compound acid having a $pK_a$ of 4.16 possesses a further disadvantageous property: dissolved or solubilized fractions can recrystallize in the acidic gastric medium. Such crystals can produce gastric irritation. Moreover, it must be assumed that a recrystallized fraction is no longer available for absorption, as at pH 1 in the gastric juice the solution equilibrium of the active compound acid is for the greatest part on the side of the undissolved substance.

For this reason, flurbiprofen-containing tablets are customarily enteric-coated. Apart from the technological cost of this coating process, account must be taken of the impaired quality of the customary coatings after storage.

For flurbiprofen, this means that the recrystallization processes above commence with inadequate enteric coatings and an appreciable restriction in the activity and the side effects described must be expected.

The knowledge newly obtained in the last years about gastric physiology and motor function of the stomach verify that monolithic pharmaceutical forms, such as non-disintegrating enteric-coated tablets and sugar-coated tablets, have a longer residence period in the stomach, depending on its state of fullness, than particles with a size of less than 2 mm. It is understandable that such large shaped articles then remain in the stomach, it being possible for gastric residence times of up to 10 hours to occur. As a result of this fact, the start of the therapeutic effect can almost not be predetermined and such a pharmaceutical form must be considered pharmaceutically as no longer up to date. As they already exhibit "slow release" as a result of long gastric residence times, according to definition such formulations must really no longer be called immediate-effect forms.

Furthermore, for poorly water-soluble substances conversion into readily water-soluble salts is proposed in the prior art. Racemic ibuprofen is, for example, supplied as a water-soluble lysine salt which, in comparison with the free active compound acid, should cause a more rapid and significantly higher blood level maximum $c_{max}$. Commercially available ibuprofen lysinate-containing tablets are not enteric-coated, so that crystallization of the active compound in the acidic gastric medium with all the abovementioned disadvantages cannot be prevented. A more rapid influx of the active compound into the biophase within an hour is therefore also not to be expected.

Flurbiprofen is only absorbed in the upper small intestine, which results in a late onset of action. With a painkiller, however, a rapid action is desired. In the case of racemic flurbiprofen, for example, the pharmacokinetic parameter $t_{max}$ of 1–2 hours means that the blood level maximum is achieved after this time. Therapeutic concentrations are only achieved after more than 4–5 hours. With knowledge of these facts it is easily understandable that a patient suffering from pain takes a second or third dose even before the onset of action of the first dose, because the desired analgesic effect apparently fails to materialize. The patient is thus exposed to the danger of an overdose.

If, in addition to this factor, the problems of the long gastric residence period of enteric-coated tablets is considered, an even greater value can result for $t_{max}$ in the case of flurbiprofen and the patient will also more likely be tempted to take a multiple dose. This problem arises to an increased extent with a full stomach, as a result of which the gastric residence time can be additionally prolonged.

The relatively rapid onset of action of a pharmaceutically well formulated acetylsalicylic acid tablet can therefore not be expected with classical pharmaceutical formulation in respect of the pharmacokinetic parameters $t_{max}$ and $c_{max}$ for flurbiprofen.

J. J. Marty et al., Pharm. Acta Helv. 53, 1 (1978) pp. 17–23 describes the preparation of gelatin nanoparticles in which active compounds can also be included. A pH adjustment during the preparation of these gelatin nanoparticles is proposed for desolvation and resolvation. Conversion of the medicament to nanoparticles is not disclosed.

EP-A-028020 describes flurbiprofen-containing pharmaceutical preparations in which the active compound, however, is not present in the form of nanoparticles.

The present invention is therefore based on the object of developing a medicament and a process for its preparation for the rapid release and influx of flurbiprofen, which largely avoid the disadvantages mentioned above for the prior art.

This object is achieved according to the invention by means of an immediate-effect medicament as in patent claim 1. This object is furthermore achieved by the use of a pharmaceutically administrable nanosol of flurbiprofen as in patent claim 20.

Customary individual doses for the flurbiprofen racemate are 200 mg to 800 mg, and in the case of S-flurbiprofen 50 mg to 400 mg are customary. Flurbiprofen is present in the context of the present invention either as a racemate, i.e. as a racemic mixture with its enantiomers, as a pseudoracemate (mixture of equal amounts of S- and R-flurbiprofen) or in a mixture of different amounts of S- and R-flurbiprofen in the range between pure S- and pure R-flurbiprofen.

In the International (PCT) Patent Application PCT/DE92/01010 of the present date having the title "Pharmazeutisch applizierbares Nanosol und Verfahren zu seiner Herstellung" (Pharmaceutically administrable nanosol and process for its preparation) of ALFATECH-Pharma GmbH, whose contents are also made the contents of the present patent application, nanosols and processes for their preparation are described which make it possible to stabilize colloidally disperse solutions of poorly water-soluble active substances by gelatin, collagen hydrolyzates or gelatin derivatives if the isoionic point (=charge equilibrium) between gelatin and the surface-charged active compound particles is at least approximately established. In this process, the system active compound particle/gelatin is brought to charge equilibrium by compensating the surface charge of the particles by a corresponding opposite charge of the gelatin molecules. This is achieved by establishment of a specific charge on the gelatin molecules which depends on their isoelectric point and the pH of the solution.

BRIEF DESCRIPTION OF THE DRAWINGS

FIG. 1 shows a schematic representation of the adjustable states of charge of gelatins as a function of the pH and IEP, it being possible for the IEP to be between 3.5 and 9.5, depending on the manner of preparation. Below pH 3.5, nearly all types of gelatin are positively charged. In the basic range above pH 9.5, all types of gelatin are negatively charged.

FIG. 2 shows the mechanism of passive pharmaceutical substance absorption in the gastrointestinal tract.

According to the invention the fact is therefore utilized that gelatins, collagen hydrolyzates or gelatin derivatives (nearly independently of the viscosity) lead to a stable colloidally disperse system in nanosol form when the isoionic state of charge is present between pharmaceutical substance particles and gelatin, collagen hydrolyzate or gelatin derivative.

On the other hand, gelatins according to the prior art were only employed for the stabilization of an inorganic, colloidally disperse system. Thus German Pharmacopeia 9 describes a colloidal injection solution of radioactive gold which is prepared with gelatin. It was merely proposed here that the macromolecule be present as a "cementing substance" between the individual colloid particles and thus particle aggregation be prevented. However, nothing was known until now about the stabilization mechanism, e.g. for pharmaceutical substances.

The International (PET) Patent Applications of the present date of ALFATEC-Pharma GmbH and PAZ Arzneimittelentwicklungsgesellschaft mbH relate to the immediate-effect form of S- and R-ibuprofen (PCT/DE92/01016), the sustained-release form of S- and R-ibuprofen (PCT/DE92/

01007), the immediate-effect form of S- and R-flurbiprofen (PCT/DE92/01008) and the sustained-release form of S- and R-flurbiprofen (PCT/DE92/01015). Their disclosure is also made the subject of the present patent application.

According to the invention, flurbiprofen racemates, the racemic mixture of its enantiomers, which consists of 50% S- and 50% R-flurbiprofen pseudoracemate, pure S- and R-flurbiprofen and mixtures of S- and R-flurbiprofen in different amounts in the range between pure S- and R-flurbiprofen, can be used as flurbiprofen.

The advantages of this novel product are thus obvious. As a result of controlled absorption of the active compound even in the stomach, the rate of influx and bioavailability of flurbiprofen which was previously to be classified as problematical on account of its poor solubility, can surprisingly be significantly improved.

In order to explain the physiological background of the absorption of pharmaceutical substances in general and the improved absorption rate of the nanosols according to the invention adequately, first a consideration of the mechanism of physiological absorption of pharmaceutical substances as is also presented in relevant publications is necessary. However, the present invention is neither tied to the following attempt at a scientific explanation of the phenomena occurring according to the invention nor can it be restricted by this.

Passive pharmaceutical substance absorption takes place according to the present state of knowledge (theory according to Brodie et al.), if the following conditions exist:

a) the gastrointestinal membrane acts as a lipid barrier, b) the pharmaceutical substance is only absorbed in dissolved and uncharged, i.e. nonionized form, c) acidic pharmaceutical substances are preferably absorbed in the stomach and basic pharmaceutical substances preferably in the intestine.

After the oral uptake of a pharmaceutical substance into the body, its absorption, i.e. the crossing into the general circulation (biophase) is prevented to a great degree by physical barriers (see FIG. 2), namely by the mucus layer and an aqueous layer adhering thereto the cell membranes of the intestinal epithelial cells with the glycocalyx covalently bonded thereto and the so-called "tight junctions" which connect the epithelial cells with one another on their apical side.

These barriers presuppose that absorption of pharmaceutical substances takes place through the lipid double layers fundamentally independently of their distribution mechanism and state of charge (so-called passive diffusion).

The epithelial cells of the entire gastrointestinal tract are covered with a mucus layer which consists of mucins (glycoproteins), electrolytes, proteins and nucleic acids. In particular, the glycoproteins form with the main components of mucus, namely water, a viscous gel structure which primarily performs protective functions for the underlying epithelial layer. The mucus layer is bound to the apical surface of the epithelial cells via the glycocalyx. The glycocalyx likewise has a glycoprotein structure which is covalently bonded to components of the membrane double layer of the epithelial cells. The branched polysaccharides of the glycocalyx, which are either directly covalently bonded to amphiphilic molecules of the double membrane or to the proteins incorporated in the double membrane, possess charged N-acetylneuraminic acid and sulfate radicals and are therefore negatively charged, which can lead to an electrostatic bond or repulsion of charged pharmaceutical substance molecules or of electrostatically charged particles respectively. The epithelial cell membranes consist of phospholipid double layers in which proteins are anchored via their hydrophobic regions. The phospholipid double layers with their lipophilic content represent a further barrier for the transport of the pharmaceutical substances to be absorbed.

From this description, it clearly follows that charged pharmaceutical substance molecules or electrostatically charged particles therefore only have a very low chance of being absorbed via the oral administration route.

The nanosols according to the invention for the first time provide the technical teaching to form a system with which these abovementioned obstacles to absorption can be overcome. As the active compound nanoparticles are stabilized in neutrally charged form by the gelatin according to the invention, they can be transported through the negatively charged glycocalyx without relatively great obstructions, in contrast to other described nanoparticles of the prior art, which are not or cannot be stabilized in neutrally charged form. According to the invention, the adjustment of the isoionic state of charge can additionally be effected in coordination with the physiological conditions. (See in particular the explanations on p. 8, lines 26–31 in combination with Examples 1 and 2).

As the active compound nanosols according to the invention can pass through the glycocalyx without obstacle, without being bonded or repelled by electrostatic effects, they thus also reach the surface of the epithelial cells and are available there in a high concentration.

Active, carrier-mediated transport mechanisms or phagocytosis can now also make a significant contribution to the absorption of the active compound nanosols.

The nanosols employed according to the invention are distinguished by high stabilities, in particular in the acidic range, without flocculating or crystallizing out. This means that the nanosol is available to the gastric mucosa for absorption for a sufficiently long period during the gastric residence period and independent of pH variations which occur, e.g. due to the effect of food.

At pHs below 2, the stability of the nanosol can be further improved by selection of a type of gelatin suited to this pH range (Example 2).

The particles of the nanosols, after their preparation, after resuspension of the dried powder and after resuspension from a pharmaceutical form, are present in particle sizes from 10 to 800 nm, preferably below 400 nm, and moreover in nearly monodisperse form. In the resuspended state, the nanosol is furthermore well dispersed in the stomach as a nanodispersion, which creates optimum conditions for absorption. As the nanoparticles are present in stabilized form, they can surprisingly be absorbed as such without them previously having to be dissolved. A solution equilibrium in advance as with micronized powders or water-soluble salts is thus unnecessary in any case. They therefore behave, looked at biopharmaceutically, as a true solution, but without being one of these.

For the first time, controlled absorption in the gastrointestinal tract is possible even during the gastric residence time as a result of the present invention. The absorption is no longer restricted to the small intestine region and a rapid influx of flurbiprofen is facilitated.

It is thus surprisingly possible to achieve for the first time with a tablet prepared according to the invention, in comparison with the prior art, a $t_{max}$ value of less than 2 h, in particular less than 1 h.

Additionally, an increase in the blood level maximum value $c_{max}$ can also be detected. The increase in $c_{max}$ can therefore in certain circumstances result in a dose reduction with the same activity.

As in vitro experiments have shown, the danger of recrystallization in the stomach and thus a delay in absorption (lag time) can be excluded as a result of the mentioned long stabilities of the nanosols according to the invention.

Furthermore, the immediate-effect form of flurbiprofen can also be combined with a sustained-release formulation of flurbiprofen.

As a particular embodiment, a powdered or granulated immediate-effect nanosol can be combined with a matrix tablet, as is described in the International (PCT) Patent Application PCT/DE92/01011 having the title "Solgesteuerte Thermokolloidmatrix auf Gelatinebasis für perorale Retardformen" (Sol-controlled thermocolloid matrix based on gelatin for oral sustained-release forms) of ALFATEC-Pharma GmbH of the same date, e.g. in a hard gelatin capsule. The contents of said patent application are also made the contents of the present patent application.

Such a pharmaceutical form initially releases the active compound rapidly and the maintenance dose (matrix tablet) constantly with high reproducibility according to a zero order rate law.

The dried nanosol can be processed to give pharmaceutical forms, for example to give a tablet, and resuspended from this. An enteric coating against the acidic gastric pH is thus superfluous.

The danger of an overdose due to taking repeatedly is excluded by the rapid onset of the analgesia as a result of absorption in the stomach. All the disadvantages and dangers of an enteric coating mentioned are inapplicable. The present invention thus also serves to increase patient compliance. This all constitutes a decisive contribution to the medicament safety demanded.

Fundamentally, the product according to the invention can be processed to give all pharmaceutical forms which are to be administered orally, in particular it can be filled into hard gelatin capsules directly as a powder. It is also outstandingly suitable for direct tableting. Processing to give beverage granules, rapidly dissolving pellets or beverage tablets is of particular interest for administration as an immediate-effect form which has a rapid influx.

In principle, the procedures and process variants mentioned in the abovementioned International Patent Application PCT/DE92/01010 "Pharmazeutisch applizierbares Nanosol und Verfahren zu seiner Herstellung" (Pharmaceutically administrable nanosol and process for its preparation), which are referred to once more in the following, are suitable for the preparation of the nanosols according to the invention:

Several processes for the preparation of the nanosols are proposed. These are an exemplary, incomplete list. The person skilled in the art can independently work out further variants in the context of the present invention on the basis of his expert knowledge:

PROCESS I

This can be used if the pharmaceutical substance is soluble in a mixture of: a water-miscible organic solvent and water, or several water-miscible organic solvents and water:

a) a gelatin selected in the preliminary tests is converted into sol form with water;

b) the pH of the solution found in the preliminary tests is adjusted;

c) one or more water-miscible, organic solvent(s), preferably ethanol, isopropanol or methanol, is/are added to this solution;

d) the pharmaceutical substance is added to the solution in solid form and dissolved;

e) the organic solvent(s) is/are removed, preferably by evaporating in vacuo; the nanosol is formed during the course of this;

f) the colloidally disperse solution is then dried, preferably by spray- or freeze-drying.

The organic solvent has the aim of dissolving the pharmaceutical substance and also changes the hydration shell of the gelatin molecules.

PROCESS II

This embodiment can be used if the pharmaceutical substance is an acid or a base whose salt is soluble in water:

a) a gelatin selected in the preliminary tests is converted into the sol form with $H_2O$;

b) a pH is set which enables formation of the salt of the pharmaceutical substance;

c) the pharmaceutical substance is dissolved in the gelatin sol with salt formation;

d) by addition of alcohol or similar organic solvents, the hydration shell of the gelatin molecules can be loosened;

e) by addition of a suitable amount of acid or base the pH is set which leads to the formation of the isoionic point (IIP) and the nanosol results;

f) the colloidally disperse solution is dried as in process I.

Stage d) is optional, but preferred.

PROCESS III

This embodiment can be used if the pharmaceutical substance is a neutral substance:

a) a gelatin sol is prepared as described in (1) a) and b).

b) a second solution is prepared from a water-miscible organic solvent, preferably ethanol, methanol, isopropanol or acetone and the pharmaceutical substance.

c) the two solutions are combined.

d) the organic solvent is removed and the colloidally disperse solution is dried.

PROCESS IV a) As described in (I) a) and b).

b) A colloidally disperse system is briefly formed with the pharmaceutical substance, but without gelatin, in a second solution.

c) The solution obtained in (b) is continuously combined with the gelatin solution.

In step (IV) c) the continuous mixing of the solutions described in (IV) a) and b) can be controlled in a time-dependent manner by on-line measurement of the particle size using a suitable process, such as e.g. by laser light scattering (BI-FOQELS On-line Particle Sizer). It is thus possible to continuously set a desired particle size.

All processes mentioned are also suitable for collagen hydrolyzates and gelatin derivatives and can be applied without problems on the industrial scale.

The essential steps can largely run in an automated manner, it also being possible to carry out processes I to III continuously. In the case of the immediate-effect form for flurbiprofen, variants No. II and III may be mentioned as preferably suitable processes.

All gelatins, gelatin derivatives, collagen hydrolyzates and fractionated gelatins, and also their mixtures are suitable for the immediate-effect forms according to the invention. Types of gelatin which have an isoelectric point (IEP) described according to the invention which is not commercially available can be prepared according to Examples I to III from the above-mentioned German Patent Application.

Compared with commercially available products, the use of gelatin which has been prepared in a special manner leads to nanosols described according to the invention having increased stability.

Examples of the preparation of grades of gelatin particularly suitable according to the invention are given below. Examples of the preparation of particularly suitable types of gelatin according to the invention with isoelectric points of 3.5 to 9.5

EXAMPLE I

Process for obtaining IEPs of 7.5 to 9.5

Collagen-containing starting material such as e.g. pig skins are treated for 12 to 20 hours with an aqueous solution of a 0.45N mineral acid, preferably sulfuric acid, in a liquor ratio of 1:1. The excess of acid is then removed by washing several times, it being possible to use sodium hydrogen carbonate to shorten the process. The extraction of the stock-rich material is carried out using hot water at 55°–80° C. at a pH of 2.5 to 4.5. At pHs below 3.5 an IEP of 8.5 to 9.5 can be achieved, at pHs above 3.5 the IEP is 7 to 8.5. In this manner, various IEPs from 7 to 9.5 can be achieved as a direct function of the pH during the extraction.

After the extraction process step, the aqueous solution is neutralized and worked up as customary.

Depending on the temperature selected during the extraction, types of gelatin having high to medium molecular weight distributions can furthermore be obtained by this process.

At temperatures of 50°–55° C., particularly highly viscous and high-bloom grades are obtained. Types of gelatin having low molecular weight or cold water-soluble gelatins can be obtained by controlled degradation with collagenases.

EXAMPLE II

Process for achieving an IEP of 4 to 7.5

The collagen-containing starting material is first washed to remove foreign substances and comminuted, and then homogeneously rendered alkaline by addition of magnesite, sodium hydroxide solution or calcium hydroxide by thorough mixing in the liquor ratio 1:1.2. The material pretreated in this way is briefly hydrolyzed by pressure hydrolysis at $1.01 \times 10^5$ to $2.02 \times 10^5$ Pa and a pH of the aqueous solution of 8–14. After hydrolysis it is immediately neutralized and the still hot aqueous gelatin solution is filtered, deionized, concentrated and dried in the usual manner.

If a weakly basic hydrolyzing agent such as magnesite is taken, an IEP of 6 to 7.5 is obtained if the reaction is carried out at $1.01 \times 10^5$ Pa. IEPs of 5 to 6 are obtained when using a dilute milk of lime suspension and when using 0.005 to 0.1N sodium hydroxide solution IEPs of 4 to 5 can be achieved.

Types of gelatin having a low degree of racemization and a low peptide content can be obtained with pressure ratios of $1.01 \times 10^5$ Pa and residence times of at most 10 min.

Medium to low molecular weight types to cold water-soluble types are produced by correspondingly longer residence times.

EXAMPLE III

Process for achieving an IEP of 3.5 to 6

Collagen-containing starting material, preferably split or ossein is subjected after the starting wash to treatment with a high-speed asher. In this case, two process variants in the liquor ratio 1:1.3 offer themselves, which either use a saturated milk of lime suspension or a 0.1 to 1N sodium hydroxide solution.

When using a milk of lime suspension, the raw material is hydrolyzed for a maximum of 3 to 4 weeks with continuous agitation. The material is then neutralized by addition of acid and washed several times. Further working up follows in the usual manner. IEPs of 4 to 6 can be obtained in this manner.

When using sodium hydroxide solution, the asher process can be shortened again, the material, depending on the degree of comminution, being hydrolyzed even after 6–12 hours at concentrations of 1N sodium hydroxide solution. Neutralization is carried out using equimolar amounts of mineral acid and the neutral salts are removed by washing several times or by deionizing the aqueous gelatin solution obtained in the extraction. In this process variant, IEPs of 3.5 to 5 can be obtained.

Particularly low-peptide types of gelatin are obtained with a short residence time in the asher. Types of gelatin with high to average molecular weight distribution ($M=10^4–10^7$ D) can thus be obtained.

Low molecular weight to cold water-soluble types of gelatin can be obtained by thermal degradation or enzymatically.

In the case of the 2-arylpropionic acid derivatives, types of gelatin having an IEP of 3.5 to 9.5 are preferably employed.

Customary pharmaceutical auxiliaries and/or other macromolecules, if they are technologically necessary, can be added to the nanosols according to the invention in the liquid or dry state.

For example, an addition of polyvinylpyrrolidone in the quantitative ratio gelatin to polyvinylpyrrolidone in the range from 5:1 to 500:1 may be suitable.

The technological processing properties of an immediate-effect form within the meaning of the invention, which is processed e.g. to give tablets or is to be lyophilized, can be improved by addition of low molecular weight types of polyvinylpyrrolidone in the range 10:1 to 50:1 without the stability of the nanosols being adversely affected.

The preferred preparation processes, procedures and names in the following examples relate as follows to the German Patent Application "Pharmazeutisch applizierbares Nanosol und Verfahren zu seiner Herstellung" (Pharmaceutically administrable nanosol and process for its preparation) (P 41 40 195.6) or the abovementioned processes and examples:

Nanosol preparation: Processes II and III
Gelatin preparation: Examples I to III
Preliminary test : see the following description:
Preliminary test:

As already mentioned at the beginning and as is evident from FIG. 1, the absolute, maximum possible net charge of an individual gelatin molecule depends mainly on the number of free COOH and $NH_2$ groups and the pH of the solution. As Type A, B, collagen hydrolyzates or gelatin derivatives differ in the number of free COOH groups, their maximum possible net charge is thus also different. With gelatin derivatives, the state of charge can additionally depend on the type of modification.

When carrying out the process according to the invention, the suitable gelatin and the suitable pH are selected in a preliminary test.

First, a working pH range suited to the physico-chemical properties of the pharmaceutical substance is selected. Physicochemical properties of the pharmaceutical substance to be taken into account in particular are: the solubility (in organic solvents or water), its properties as an acid, base or neutral substance and its stability to acids and alkali solutions.

In a first rapid test it is determined what charge the precipitated particles have. This results, taking into account the working pH range, in the choice of a suitable type of gelatin. If the particles are, for example, negatively charged, a gelatin is picked which is positively charged under the given pH conditions. This rapid test for the determination of the particle charge has the advantages that it can be carried out without a great outlay in terms of apparatus and time. A time-consuming and inaccurate zeta potential measurement can thus be dispensed with entirely.

In many cases, it will be adequate for this rapid test to convert two commercially available Type A and B gelatins with an IEP of 9.5 or 3.5 respectively and with peptide contents of <30% and a bloom number of 200, which are additionally designated as standard gelatins, into the sol form at a pH of 6 (5% strength aqueous solution) and to dissolve the pharmaceutical substance in a water-miscible solvent, such as e.g. ethanol, isopropanol or acetone, and in each case to mix homogeneously with the gelatin solutions. At the same dose of the pharmaceutical substance, in the case of the gelatin which is unsuitable in its state of charge a colloidal system will either not form or immediately become unstable or the pharmaceutical substance will flocculate. If the resulting particles are negatively charged, they are stabilized earlier by the gelatin solution of Type A, which is positively charged at a pH of 6, than by the solution containing Type B gelatin; in contrast, in this case Type B either no colloidal system will form or the system will immediately destabilize. The flocculation of the particles can be monitored e.g. via a simple turbidity measurement.

In this rapid test, the working pH range must be taken into account in each case. Other gelatins can also be selected as a standard, but they must be selected in their IEP such that they carry an opposite net charge at this pH (see also FIG. 1). In most cases, said standard Type A and B gelatins are adequate for this rapid test.

Starting from the result of the preliminary experiment, the optimum conditions for the formation of the nanosols are determined by stepwise variation of the IEPs by use of appropriate types of gelatin and of the pH of the solution in relatively small ranges (e.g. 0.1 pH steps), i.e. the stability optimum which is characterized by the isoionic point (IIP) must be found in order to guarantee an adequate stability for the pharmaceutical applications mentioned.

It can be the case that a stability of the nanosols which is acceptable within the meaning of the invention is already found in a relatively narrow pH range (about 0.5 units) around the isoionic point, so an adjustment of this point itself is not absolutely necessary. On the other hand, several gelatins can also lead to the same, stable results. Thus, for example (Example 5) with the oral antidiabetic glibenclamide in the case of a Type B gelatin with an IEP of 5.5 the stability optimum can be at a pH of 3.2, while in the case of a Type B gelatin with an IEP of 3.8 the stability optimum is at a pH of 2.2.

Characterized by a stability maximum, in both cases the isoionic point was reached (the dependence of the net charge on the pH and the IEP must be non-linear, as it is given by the $pK_a$ value of the COOH or $NH_3^+$ groups present).

Gelatin is a scleroprotein obtained from collagen-containing material which has differing properties according to the preparation process. Molecular weight ranges from a few thousand D up to a few million D exist, which can be very different in their molecular weight composition and in their physicochemical behavior. With exact knowledge of these relationships, novel pharmaceutical applications can be found which are distinguished by high reproducibility and simple technological processing. Details can be taken from the abovementioned applications. With a particularly gentle preparation procedure, types of gelatin can be obtained which only have a low content of dextrorotatory amino acids and are thus constructed similarly to the native collagen molecule. These gelatins are distinguished, for example, by particularly good stability properties for nanosols. Such a gelatin is advantageously suitable according to the invention. Depending on the working up of the raw material (acidic or basic hydrolysis), gelatins are obtained whose isoelectric points are very different. By means of special preparation techniques, isoelectric points can be produced specifically, it being possible to suit the molecular weight distribution to the application.

Depending on the gelatin preparation procedure (extent of breakdown of native collagen and acidic or alkaline hydrolysis process), gelatin of Type A or Type B has a characteristic molecular weight spectrum or molecular weight distribution. Table 1 indicates the molecular weight distributions of various types of gelatin or of collagen hydrolyzates, and the percentage content (frequency) of individual molecular weight ranges.

TABLE 1

Molecular weight distribution of various known types of gelatin or of known collagen hydrolyzates

| Molecular Mass Distribution (kD) | Native Collagen % | Gelatin Type B % | Gelatin Type A % | Collagen hydrolyzate Gelita ® Collagel A | Collagen hydrolyzate Gelita ® Collagel B | Collagen hydrolyzate Gelita ® Sol C | Elastin hydrolyzate Gelita ® Gelasatin |
|---|---|---|---|---|---|---|---|
| >360 | 100 | 18.0 | 18.0 | 0 | 0 | 0 | 0 |
| 285 | 0 | 7.0 | 9.0 | 0 | 0 | 0 | 0 |
| 145–237 | 0 | 20.0 | 34.0 | 1.0 | 1.5 | 0 | 0 |
| 95 | 0 | 26.0 | 11.0 | 0 | 0 | 0 | 0 |
| 95–50 | 0 | 16.3 | 13.4 | 2.6 | 4.0 | 1.1 | 0 |
| 50–20 | 0 | 7.4 | 9.1 | 18.0 | 14.5 | 0.3 | 0 |
| 20–10 | 0 | 3.9 | 3.8 | 43.0 | 31.5 | 3.7 | 0.2 |
| 10–5 | 0 | 3.0 | 3.0 | 15.4 | 20.0 | 12.2 | 5.2 |
| 5–2 | 0 | 0 | 0 | 6.0 | 14.0 | 26.0 | 93.9 |
| 2–1 | 0 | 0 | 0 | 7.0 | 8.0 | 23.0 | 0 |
| <1 | 0 | 0 | 0 | 6.5 | 7.0 | 34.0 | 0 |
| MW | 360 | 165 | 185 | 12–18 | 12–18 | 3 | 2–3 |

The predominance of an individual range compared with the other molecular weight ranges of the same gelatin can be seen clearly in the individual columns. This range is thus the maximum of the molecular weight distribution (it is 95 kD e.g. for the Type B gelatin shown in the figure). The concept of the "maximum of the molecular weight distribution", however, is to be separated strictly from the concept of the "average mean molecular weight". This mean value is 165 kD for the gelatin of the Type B mentioned.

In the case of R-flurbiprofen, in particular at relatively high dosage, types of gelatin are preferably suitable which have a content of dextrorotatory amino acids of below 20% and whose maximum in the molecular weight distribution is below $10^5$ D. For the preparation of tablets, as is customarily predominant with painkillers, types of gelatin having bloom values of 0–50 are preferably suitable. With the gelatins mentioned, a weight ratio of gelatin to active compound of 0.5:1 to 3:1 can advantageously be maintained.

In the formulation of immediate-effect or sustained-release preparations, the pharmacist makes a fundamental distinction between:
1. pharmaceutical preparation, i.e. of a release of the pharmaceutical substance, e.g. from a tablet in a manner which is rapid (immediate-effect form) or prolonged (sustained-release form) timewise;
and
2. the pharmaceutical substance-specific absorption site, such as e.g. the stomach or specific sections of the intestine.

The nanosols according to the invention are able, independently of the pharmaceutical preparation, to be absorbed in the entire gastrointestinal region on account of their special composition. They can therefore be advantageously processed to give immediate-effect or sustained-release pharmaceutical forms.

Commercially available gelatins, fractionated gelatins, collagen hydrolyzates and gelatin derivatives, in particular those types which are characterized by a low bloom number of 0 (cold water-soluble gelatins or collagen hydrolyzates) up to 240 bloom, preferably 0 to 170 bloom, are also suitable for the nanosols used according to the invention.

In the case of flurbiprofen, types of gelatin with IEPs of 3.5 to 7.5 are preferably employed.

For spray- or freeze-drying of R-flurbiprofen nanosols, addition of polyvinylpyrrolidone (PVP) to the aqueous gelatin solution, in particular PVP K 15 or PVP K 25 in the weight ratio from 1:5 to 1:30 has been shown to be advantageous, a readily pourable powder being obtained without adverse effect on the stability of the nanosol.

A particular embodiment of the present invention provides for a special combination, consisting of a rapid influx R-flurbiprofen nanosol and an S-flurbiprofen nanosol in sustained-release form, in a pharmaceutical form having the following advantages for rheumatism therapy:
1. Owing to the rapid influx of the R-flurbiprofen nanosol immediate-effect form, the rheumatism patient also obtains rapid freedom from pain.
2. As a result of the delayed release of the anti-inflammatory S-flurbiprofen nanosol, a constant plasma level is immediately obtained and maintained which, over the appropriate period of time, can effect the inhibition of inflammation and detumescence of the tissue concerned without variations.

A coated or two-layer tablet known per se is advantageous as the pharmaceutical form. It is also possible to fill two shaped articles into a hard gelatin capsule.

The processes and procedures according to the invention referred to in the examples correspond to the processes and procedures described above.

EXAMPLE 1

Active compound: R-flurbiprofen, enantiomerically pure active compound acid
  Gelatin type: Commercially available, Type B, 20 bloom
  Nanosol preparation: analogously to Process II
  Weight ratio gelatin/active compound: 3:1
  The working pH range for R-flurbiprofen is below its $pK_a$ of 4.16.

After carrying out the preliminary test according to the invention and the following series of measurements, a stability maximum is achieved at a pH of 3.2 using a Type B gelatin (IEP 4.5).

600 g of gelatin specified above are dissolved in 10 l of water. 200 g of R-flurbiprofen are dissolved in 700 g of sodium hydroxide solution (10% strength) and added to the gelatin solution. The mixture is then adjusted to pH 3.2 by addition of hydrochloric acid, whereupon the nanosol forms.

Particle size measurements (BI-FOQUELS On-line Particle-Sizer) show average particle sizes of the nanosol of less than 320 nm.

It is concentrated in the customary manner and spray-dried.

The nanosol powder is pressed with addition of customary tableting auxiliaries in an eccentric press to give rapidly dissolving tablets with a content of R-flurbiprofen of 50 mg.

Under in vitro test conditions (900 ml of 0.1N HCl, paddle, 100 rpm, 37° C.), particle growth commences after 10 hours.

EXAMPLE 2

A nanosol as described in Example 1 is prepared, but a gelatin having an IEP of 3.7 is selected which shows a stability maximum at pH 1.9.

Under the same test conditions as in Example 1, a stability of the nanosol which is increased by 20% results.

EXAMPLE 3

The procedure is as described in Example 1. The spray-dried R-flurbiprofen nanosol, however, is mixed with customary fillers and filled into hard gelatin capsules at a dose of 25 mg per capsule.

EXAMPLE 4

Analogously to Example 1; except that 30 g of polyvinylpyrrolidone (PVP K 15) are added to the gelatin sol.

The nanosol is concentrated in the customary manner and spray-dried and, after mixing with customary auxiliaries, pressed in an eccentric press to give tablets with a content of R-flurbiprofen of 50 mg per tablet.

In a dissolution test according to USP XXII (900 ml of water, paddle, 65 rpm, 37° C.), a dissolving time of the tablets of under 10 minutes is determined. In comparison with this, tablets from the batch according to Example 1 are investigated under identical conditions and show dissolving times which are higher on average by 30%.

EXAMPLE 5

R-flurbiprofen beverage granules

Active compound: R-flurbiprofen, enantiomerically pure active compound acid

Gelatin type: Type B, cold water-soluble, preparation Example II

Nanosol preparation: analogously to Process III

Weight ratio gelatin/active compound: 20:1

The stability optimum after the preliminary tests according to the invention and series of measurements shows a gelatin having an IEP of 4.5 at a pH of 3.2.

600 g of the above type of gelatin are dissolved in 6 l of water and adjusted to pH 3.2 using hydrochloric acid. 30 g of R-flurbiprofen are dissolved in 0.3 l of ethanol. Both solutions are combined, the organic solvent is removed in vacuo and the nanosol is worked up in the customary manner and spray-dried. The powder obtained is granulated and filled with a content of R-flurbiprofen of 100 mg per individual capsule. The granules dissolve in water at 20° C. within 3 minutes.

I claim:

1. An immediate-effect medicament for the treatment of painful and/or inflammatory, and also febrile, disorders, containing flurbiprofen in addition to customary pharmaceutical excipients and auxiliaries, wherein the flurbiprofen is present in the form of a pharmaceutically administrable nanosol which contains gelatin, a collagen hydrolyzate or a gelatin derivative as the excipient, the nanosol
   a) having an inner phase of flurbiprofen which has a particle size of 10–800 nm and possesses a surface charge,
   b) an outer phase of gelatin, a collagen hydrolyzate or a gelatin derivative, which is oppositely charged, and
   c) an approximate or complete isoionic state of charge of the inner and outer phase and
   d) being physiologically absorbable.

2. A medicament as in claim 1, wherein the flurbiprofen is present as a racemate.

3. A medicament as in claim 1, wherein the flurbiprofen is present as a pseudoracemate or as a mixture of the racemate with its enantiomers.

4. A medicament as in claim 1, wherein the flurbiprofen is present as pure S- or R-enantiomer.

5. A medicament as in claim 1, wherein the flurbiprofen is present as a mixture of S- and R-enantiomers of different content.

6. A medicament as in claim 3, wherein the flurbiprofen is present in the form of a mixture of previously separated enantiomers.

7. A medicament as in claim 1, wherein the flurbiprofen is present as a liquid, aqueous nanodispersion.

8. A medicament as in claim 1, wherein the flurbiprofen is present as a solid, resuspensible nanodispersion.

9. A medicament as in claim 6, wherein the flurbiprofen has an average particle size of below 400 nm.

10. A medicament as in claim 1, wherein the gelatin has a maximum in the molecular weight distribution of below $10^5$ D and bloom values of 0–240.

11. A medicament as in claim 1, wherein the gelatin has a bloom value of 0–170.

12. A medicament as in claim 11, wherein the gelatin has a peptide content of 50–90%.

13. A medicament as in claim 1, wherein the gelatin has a content of dextrorotatory amino acids of below 20%.

14. A medicament as in claim 1, wherein the weight ratio of gelatin to active compound is 0.5:1 to 10:1.

15. A medicament as in claim 1, comprising an outer phase of the nanosol which additionally contains polyvinylpyrrolidone in a weight ratio of gelatin to polyvinylpyrrolidone is 5:1 to 500:1.

16. A medicament as in claim 1, wherein the pharmaceutical form is a rapidly dissolving tablet.

17. A medicament as in 1, wherein the pharmaceutical form is a rapidly dissolving powder or granules.

18. A medicament for the treatment of painful and/or inflammatory, and also febrile, disorders, containing flurbiprofen in addition to suitable pharmaceutical excipients and auxiliaries, wherein the medicament is partly present as an immediate-effect form and partly as a sustained-release form containing flurbiprofen in the form of a pharmaceutically administrable nanosol, the nanosol
   a) having an inner phase of flurbiprofen which has a particle size of 10–800 nm and possesses a surface charge, b) effective amounts of an outer phase of gelatin, a collagen hydrolyzate or a gelatin derivative, which is oppositely charged wherein the immediate-effect form is characterized by being comprised of a gelatin, a collagen hydrolyzate or a gelatin derivative that has a bloom number between 0 to 240, and c) an approximate or complete isoionic state of charge of the inner and outer phase and d) being physiologically absorbable.

19. A medicament as in claim 18, wherein the pharmaceutical form is a hard gelatin capsule containing a rapidly dissolving powder of flurbiprofen as the immediate-effect form and a slowly dissolving tablet of flurbiprofen as the sustained-release form.

20. A method of preparing an analgesic and/or antirheumatic and/or antipyretic which comprises employing a pharmaceutically administrable nanosol of flurbiprofen, the nanosol a) having an inner phase of flurbiprofen which has a particle size of 10–800 nm and possesses a surface charge, b) an outer phase of gelatin, a collagen hydrolyzate or a gelatin derivative, which is oppositely charged, and c) an approximate or complete isoionic state of charge of the inner and outer phase and d) being physiologically absorbable, so that said analgesic and/or antirheumatic and/or antipyretic is an immediate effect medicament.

* * * * *